United States Patent [19]
Matsui et al.

[11] Patent Number: 6,140,723
[45] Date of Patent: Oct. 31, 2000

[54] VIBRATION GENERATING DEVICE AND ORAL HYGIENE DEVICE USING SAME

[75] Inventors: Tsuguo Matsui, Kyoto; Michihisa Sugimoto, Higashiosaka; Masaharu Kita, Takatsuki, all of Japan

[73] Assignee: Sunstar Inc., Takatsuki, Japan

[21] Appl. No.: 09/142,057

[22] PCT Filed: Mar. 21, 1997

[86] PCT No.: PCT/JP97/00959

§ 371 Date: Sep. 17, 1998

§ 102(e) Date: Sep. 17, 1998

[87] PCT Pub. No.: WO97/34710

PCT Pub. Date: Sep. 25, 1997

[30] Foreign Application Priority Data

Mar. 21, 1996 [JP] Japan ..................................... 8-064137

[51] Int. Cl.[7] .................................................... H02K 7/06
[52] U.S. Cl. ................ 310/81; 310/47; 310/48; 310/75 A; 310/75 B; 310/75 C; 310/75 D; 310/103; 310/156; 15/22.1; 15/22.2; 15/22.3; 15/22.4; 15/23; 15/24; 74/87
[58] Field of Search .................. 310/81, 47, 48, 310/75 A, 75 B, 75 C, 75 D, 103, 156; 15/22.1–4, 21.1, 23, 24, 28; 74/87; 340/311.1; 30/44, 45

[56] References Cited

U.S. PATENT DOCUMENTS

| | | | |
|---|---|---|---|
| 3,831,537 | 8/1974 | Siegel | 112/220 |
| 5,504,959 | 4/1996 | Yukawa et al. | 15/22.1 |
| 5,590,434 | 1/1997 | Imai | 15/22.1 |
| 5,651,157 | 7/1997 | Hahn | 15/22.1 |
| 5,697,117 | 12/1997 | Craft | 15/22.1 |
| 5,794,295 | 8/1998 | Shen | 15/22.1 |

*Primary Examiner*—Elvin Enad
*Assistant Examiner*—Thanh Lam
*Attorney, Agent, or Firm*—Armstrong, Westerman, Hattori, Mcleland & Naughton

[57] ABSTRACT

An oral hygiene device comprises a rotating body 22 mounted to a rotating shaft 21 of an electric motor 14, an output shaft 11 resiliently supported via a resonance pin 25 to be swingable finely, a drive magnetic body 23 provided on the rotating body 22, and a driven magnetic body 31 provided on the output shaft 11 to face the drive magnetic body 23 so as to be out of contact therewith. The drive magnetic body 23 and the driven magnetic body 31 are composed of permanent magnets, and as the rotating body 22 revolves, a varying magnetic field is generated between the both magnetic bodies 23, 31 to cause vibration of the output shaft 11 at high speed. In this manner, there are provided a vibration generating device, which can be manufactured at low cost and efficiently transmits vibration, and an oral hygiene device using the same.

8 Claims, 18 Drawing Sheets

(a)

(b)

(a)

(b)

(c)

VIBRATION GENERATING DEVICE AND ORAL HYGIENE DEVICE USING SAME

TECHNICAL FIELD

The present invention relates to a vibration generating device for generating a vibration using an electric motor, and an oral hygiene device using the same.

BACKGROUND ART

As the oral hygiene device, for example, in an electric toothbrush there are known a first type electric toothbrush in which a vibration is applied to a replacement brush by rotating an eccentric weight by an electric motor, a second type one in which a rotary motion of an electric motor is converted to a liner motion through a cam or the like, thereby reciprocating the replacement brush, and a third type one in which, as disclosed in Japanese Patent Unsearched Publication No. 7-505069, DC current supplied from a battery or the like is converted to AC current by an invertor and supplied to a coil, thereby vibrating the replacement brush by alternating field of the coil.

Although the first type electric toothbrush has a simple structure and can be produced at low cost, since the vibration is transmitted to the replacement brush through a casing for accommodating the electric motor and battery, a part of the vibration is transmitted to fingers via the casing, so that a sufficient amplitude at hair tips of the replacement brush cannot be obtained and, therefore, there is a problem that eventually it performs only a supplemental action for manual brushing. Further, since vibration frequency of the replacement brush becomes the same as a rotation number of the electric motor, the vibration frequency of the replacement brush is difficult to be changed.

Although the second type electric toothbrush can provide a vibration which is more similar to actual brushing because the rotary motion of the electric motor is mechanically converted to the linear reciprocating motion using a cam or the like, the structure is complicated and production cost becomes high and, in addition, it is considered that if a large load is applied to the replacement brush, the electric motor is overloaded, so that it may be damaged. Further, it involves a problem that if the reciprocating speed is increased, the mechanical loss is increased.

Although the third type electric toothbrush can considerably enhance cleaning performance by easily increasing the vibration frequency of the replacement brush, the invertor or the like is necessary. Therefore, there are problems that production cost rises and power consumption is also increased.

An object of the present invention is to provide a vibration generating device which is capable of effectively transmitting a high speed vibration and which can be produced at low cost, and an oral hygiene device using the same.

DISCLOSURE OF THE INVENTION

A vibration generating device according to claim 1 is one comprising a rotating body mounted on a rotary shaft of an electric motor, a driving magnetic body provided in the rotating body, an output member resiliently supported so as to be swingable finely, and a driven magnetic body provided in the output member to face said driving magnetic body so as not to contact therewith, wherein at least one of the driving magnetic body and the driven magnetic body is composed of a permanent magnet or an electromagnet and the output member is vibrated by a varying magnetic field generated between both magnetic bodies with a rotation of the rotating body.

Therefore, by rotating the rotating body by means of the electric motor, the driven magnetic body provided in the rotating body repeatedly faces the driven magnetic body provided in the output member. As a result, by a varying magnetic field acting between the driving magnetic body and driven magnetic body, the rotating motion of the rotating body is converted to vibration of the output member, so that it follows that the output member is vibrated depending on the rotation number of the electric motor.

As recited in claim 2, it is preferable that the driving magnetic body and the driven magnetic body are composed of a permanent magnet or an electromagnet and both magnetic bodies are arranged such that the same poles thereof face each other. That is, since forces which mutually repulse act between both magnetic bodies, even if there is a slight looseness in support of the rotating body and the output member, there never occurs a disadvantage that the driving magnetic body comes into an intimate contact with the driven magnetic body.

As recited in claim 3, it is permissible that the frequency of the varying magnetic field is set to a resonant frequency of a combined body consisting of the output member and a member which is mounted on the output member and vibrated together with the output member. In this case, it follows that the combined body resonant with the varying magnetic field acting between the driving magnetic body and the driving magnetic body and it vibrates greatly.

As recited in claim 4, it is permissible that there is provided an adjusting means for adjusting a distance between the driving magnetic body and the driven magnetic body. In this case, by adjusting the distance between both magnetic bodies by means of the adjusting means, the amplitude is changed. Concretely, if the distance between both magnetic bodies is increased, the vibration of the output member becomes weak, and if the distance between both magnetic bodies is decreased, the vibration of the output member becomes strong.

As recited in claim 5, it is permissible that the driving magnetic body is fixed eccentrically from a rotary axis of an electric motor and the driven magnetic body is provided so as to face a rotating locus of the driving magnetic body. By constituting in this manner, it is possible to easily generate a varying magnetic field between the driving magnetic body and the driven magnetic body.

As recited in claim 6, it is preferable that an elastic supporting point of the output member is set at a position substantially corresponding to a center of gravity of the combined body consisting of the output member and the member which is mounted on the output member and vibrated together with the output member. If constituted in this manner, it follows that the combined body is vibrated with its center being set at the to position substantially corresponding to center of gravity, so that the rotating motion of the rotating body is effectively converted to vibration of the output member.

As recited in claim 7, it is permissible that as the output member there is used a shaft whose tip side portion is disposed on the same axis as the rotary axis of the electric motor and whose intermediate portion is bent at a base end side than the elastic supporting point such that the driven magnetic body fixed to a base end portion faces a rotating locus of the driving magnetic body. In this case, it becomes possible that the output member, the rotating body and the electric motor can be compactly constituted in the radial direction of the rotary axis. Further, it follows that the tip portion of the shaft as an output member is greatly vibrated.

As recited in claim 8, it is permissible that two permanent magnets are provided as the driving magnetic body and one permanent magnet is provided as the driven magnetic body. In this case, it follows that the output member is vibrated at a frequency twice the rotation number of the electric motor.

An oral hygiene device according to the invention is one wherein an oral hygiene tool is removably attached directly or indirectly to the output member of the vibration generating device.

That is, by attaching the oral hygiene tool directly or indirectly to the output member of the vibration generating device, it follows that the teeth is brushed, the interdental gap are cleaned or the gingiva is massaged.

BRIEF DESCRIPTION OF THE DRAWINGS

FIG. 10(*b*) is an explanatory view showing a motion of a brush of the same electric toothbrush;

FIG. 13(*b*) is a partially broken side view of a portion in the vicinity of the output shaft of the same electric toothbrush;

BEST MODE FOR CARRYING OUT THE INVENTION

Hereinafter, an embodiment of the present invention will be described with reference to the accompanying drawings.

This embodiment is one in which the present invention is applied to a vibration generating device of an electric toothbrush.

Figure 1:
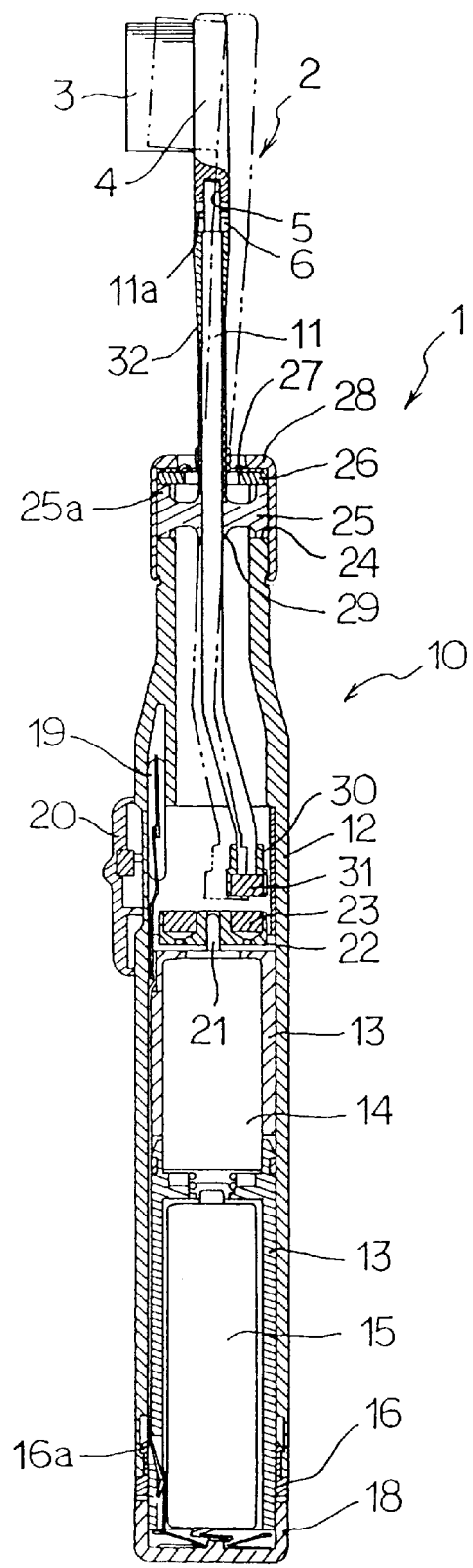
FIG. 1 is a longitudinal sectional view of an electric toothbrush according to the present invention.
Figure 2:
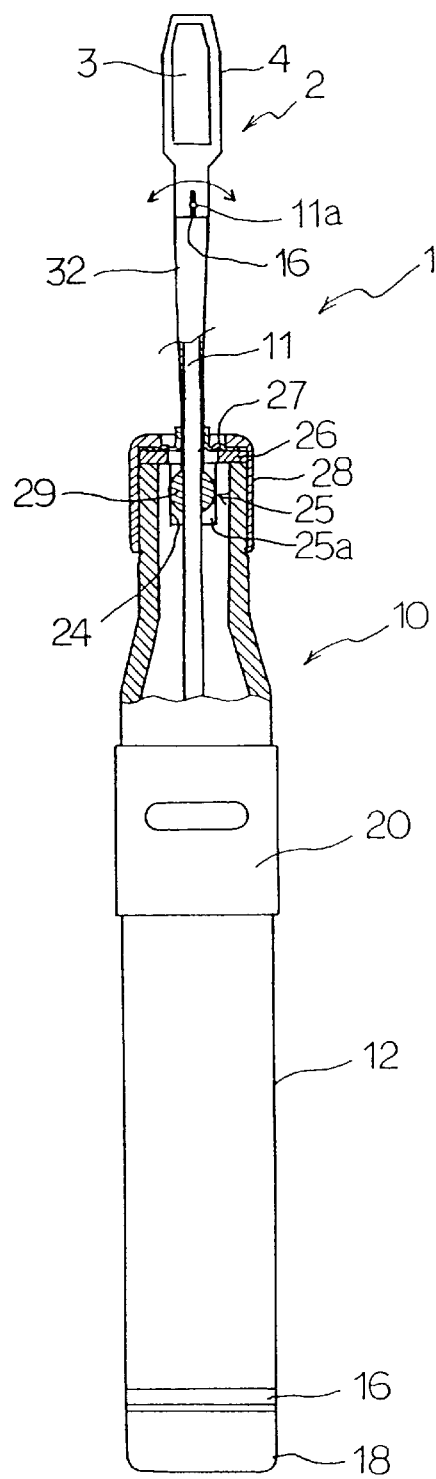
FIG. 2 is a longitudinal sectional front view of a main portion of the same electric toothbrush.
Figure 3:
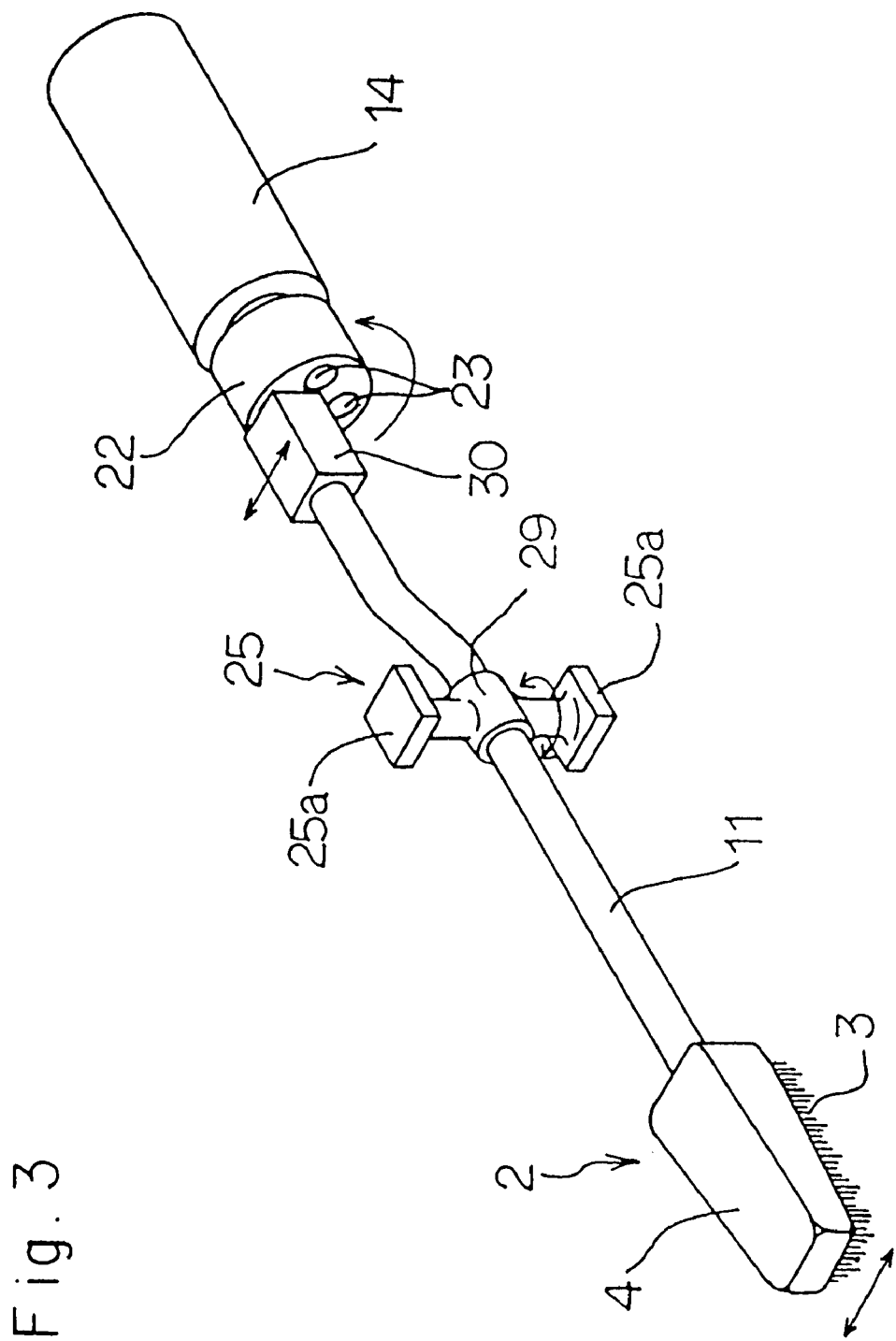
FIG. 3 is an entire structural diagram of a driving section of the same electric toothbrush.
Figure 4:
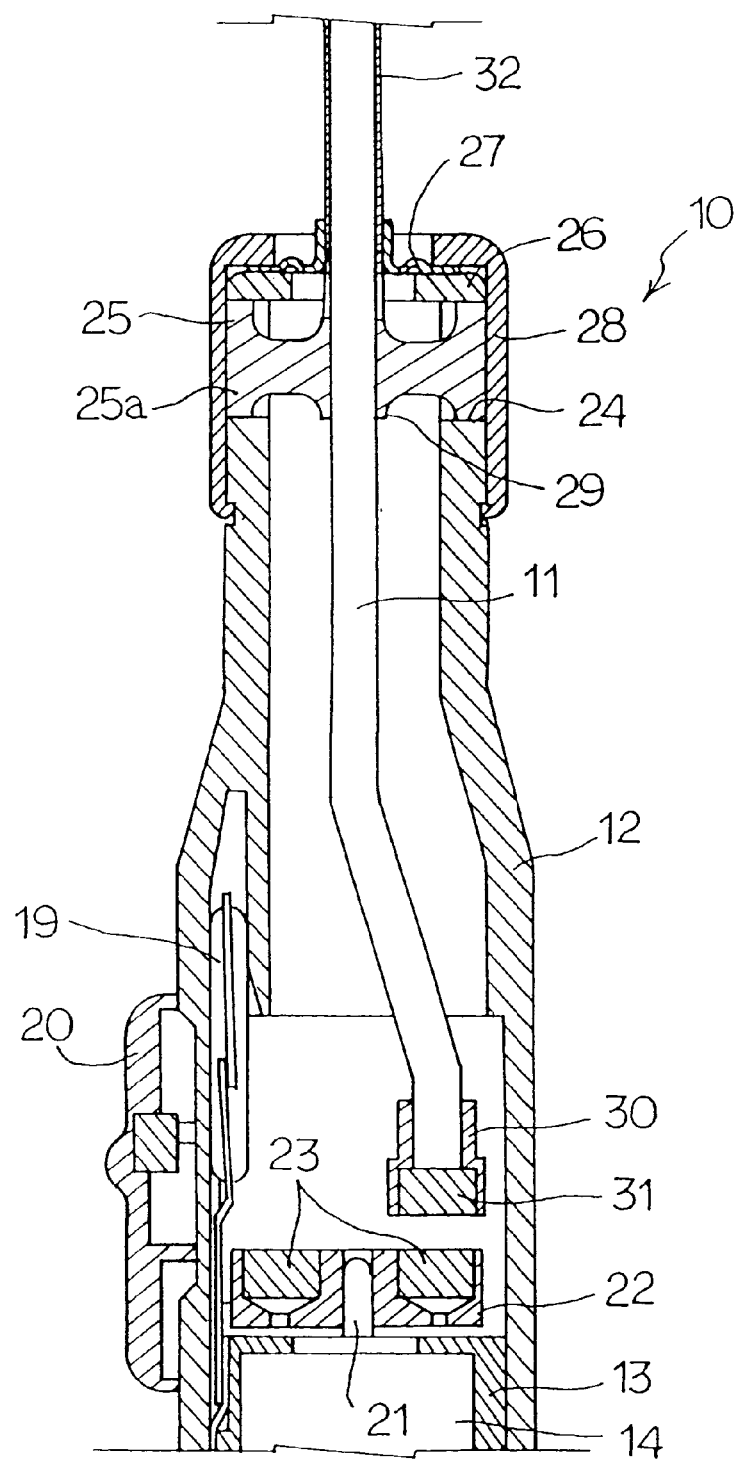
FIG. 4 is a longitudinal sectional view of an upper half portion of the same electric toothbrush.

As shown in FIGS. 1 and 2, the electric toothbrush 1 comprises basically a vibration generating device 10 and a replacement brush 2 removably mounted to an output shaft 11 which is an output member of the vibration generating device 10.

In explaining the vibration generating device 10, as shown in FIGS. 1–8, a substantially cylindrical casing 12 is provided and in a lower half portion of the casing 12 there are accommodated and held an electric motor 14 and a battery 15 through a holder member 13, which can be divided to upper and lower parts, such that they are movable up and down integrally.

Figure 5:
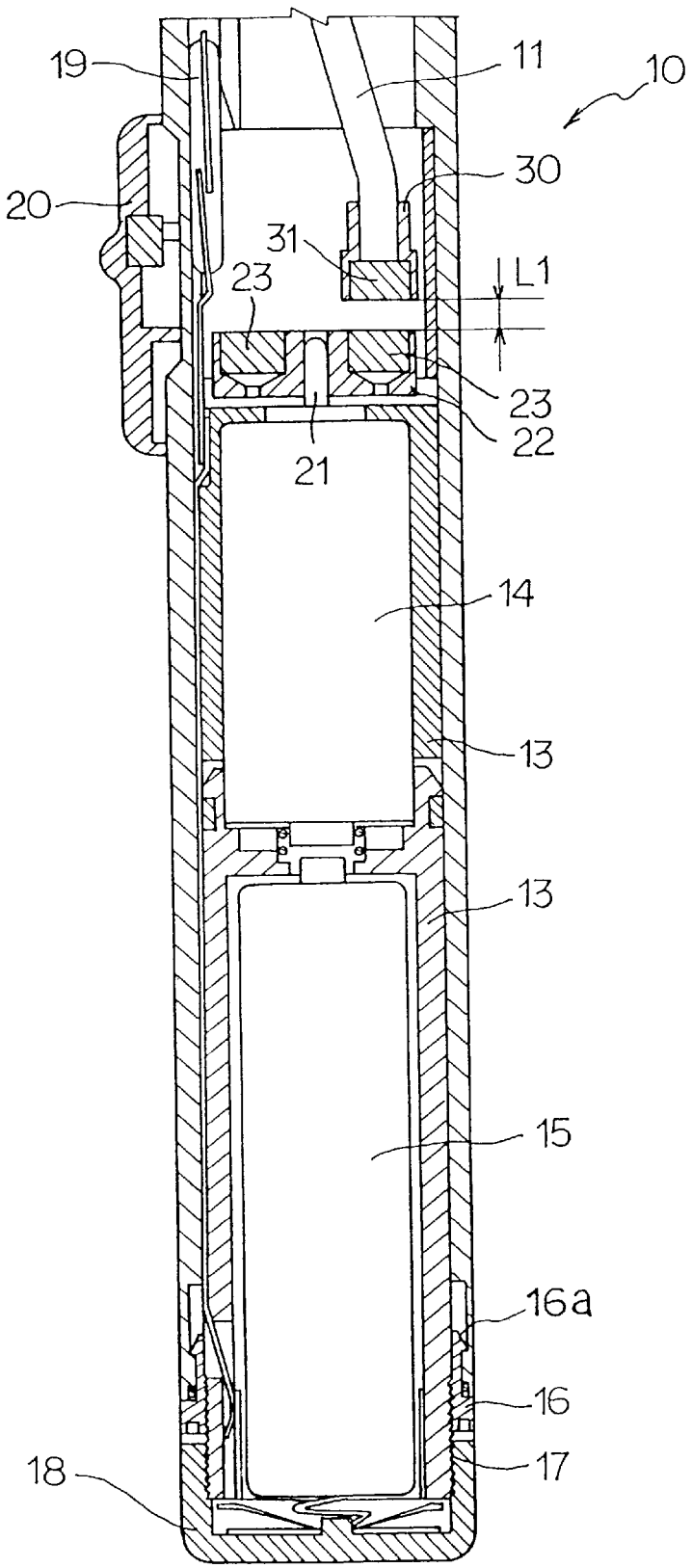
FIG. 5 is a longitudinal sectional view of a lower half portion of the same electric toothbrush.
Figure 6:
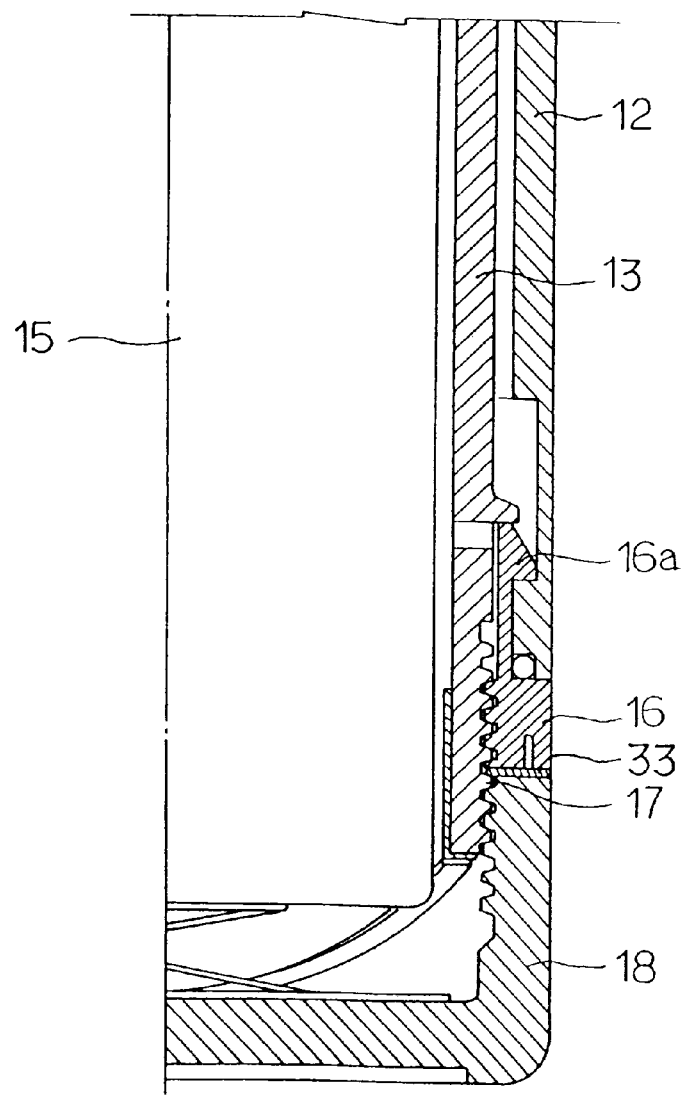
FIG. 6 is a longitudinal sectional view of a portion in the vicinity of an adjusting ring of the same electric toothbrush.
Figure 7:
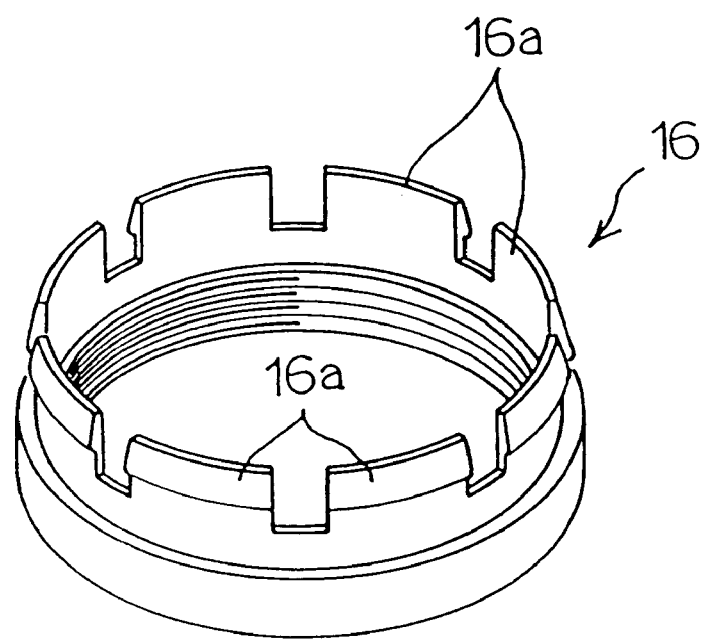
FIG. 7 is a perspective view of the adjusting ring of the same electric toothbrush.
Figure 8:
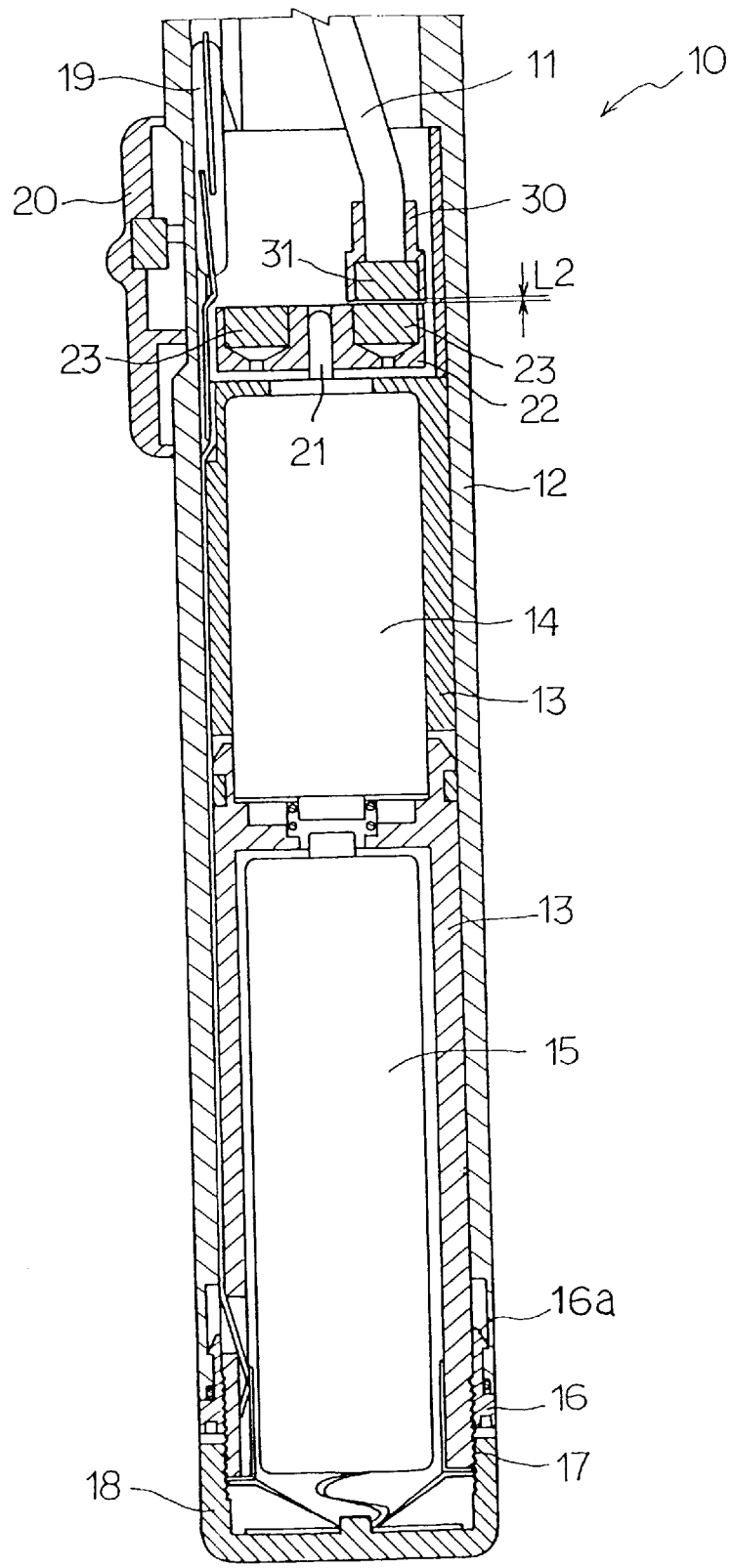
FIG. 8 is an explanatory view when adjusting a vibration strength of the same electric toothbrush.

At a lower end portion of the casing 12 there is mounted an adjusting ring 16 through a plurality of pawl portions 16a in fluid-tight condition such that it is unmovable up/down and rotatable. A threaded portion 17 is formed in the vicinity of a lower end of the holder member 13 and an intermediate portion of the threaded portion 17 meshes with the adjusting ring 16. That is an up/down motion of the holder member 13 in the casing 12 is restricted through the adjusting ring 16. And as shown in FIGS. 5 and 8 the holder member 13 is incorporated in the casing 12 so that the position of the holder member 13 in the casing 12 can be adjusted finely in the vertical direction by turning the adjusting ring 16. The holder member 13 and adjusting ring 16 constitute the adjusting means.

A cap member 18 meshes with the threaded portion 17 of the holder member 13 and a lower end portion of the casing 12 is closed in fluid-tight condition through a packing 33 (see FIG. 6) by this cap member 18.

The holder member 13 is provided with wiring for turning on electricity to the electric motor 14. A lead switch 19 is disposed midway of this wiring. An operation of sliding a switch button 20 disposed on a periphery of the casing 12 turns on/off the electric motor 14.

A substantially circular rotating body 22 is mounted on a rotary shaft 21 of the electric motor 14. Mounting holes whose top is open are formed at positions which are divided equally by four along the circumference of the rotating body 22 and a driving magnetic body 23 made of permanent magnet is mounted on each of the four mounting holes.

On a top portion of the casing 12 there are formed a pair of cutout portions 24 extending in back and forth to back and a resonance pin 25 made of torsion bar extending in back and forth direction is provided as a supporting member such that it stretches over the top portion of the casing 12. A fixing portion 25a having a flat shape is formed on both end portions of the resonance pin 25. The resonance pin 25 is assembled unrotatably to the casing 12 by fitting this fixing portion 25a to the cutout portion 24. On the top end portion of the casing 12 there is fixed a cap member 28 under such a condition that a washer 26 and an outer periphery of a sealing film 27 are nipped therebetween. The resonance pin 25 is fixed to the casing 12 via this cap member 28 such that it is not movable vertically. A boss portion 29 is formed on an intermediate portion of the resonance pin 25 in the length direction and the output shaft 11 extending vertically is inserted through and fixed to the boss portion 29. The output shaft 11 is assembled to the casing 12 so as to be swingable finely in the left and right direction as shown by an arrow in FIG. 2. Incidentally, reference numeral 32 denotes a cover member for the output shaft 11. The cover member 32 is composed of resilient member such as synthetic resin or synthetic rubber, so that even if it strikes a tooth, it never gives a strong impact thereto.

The output shaft 11 extends upward such that it passes through the sealing membrane 27 in fluid-tight condition and at its upper end portion there is removably attached the replacement toothbrush 2. A lower half portion of the output shaft 11 is gently bent backward in crank form so that its end faces a front portion of rotating locus of the driving magnetic body 23. A fixture 30 is fixed to the lower end portion of the output shaft 11. A mounting hole whose bottom end is open is formed on a lower half portion of the fixture 30 and a driven magnetic body 31 is assembled to this mounting hole such that it faces the driving magnetic body 23 with a slight gap being kept therebetween.

The driven magnetic body 31 and driving magnetic body 23 are made of a permanent magnet or an electromagnet. Both magnetic bodies 23, 31 are assembled to the rotating body 22 and fixture 30 respectively so that their same poles face each other. In this manner, since the four driving magnetic bodies 23 and one driven magnetic body 31 are used, it follows that the output shaft 11 is vibrated under a frequency four times the rotation number of the electric motor 14. However, it is permissible to assemble the driven magnetic body 31 and driving magnetic body 23 under such a condition that different poles face each other or that the same poles and different poles face alternately. Further, at least one of the driving magnetic body 23 and the driven magnetic body 31 may be composed of a ferromagnetic body such as iron, nickel, cobalt or alloy thereof, which can be attracted by a magnet. Further, number of the driving magnetic body 23 and driven magnetic body 31 may be determined arbitrarily. Further, in case that the driving magnetic body 23 and the driven magnetic body 31 are respectively provided in plural number, by setting a pitch between the adjacent driven magnetic bodies 31 to an integer time of the pitch between the driving magnetic bodies 23, plural driven magnetic bodies 31 can be caused to face the driving magnetic bodies 23 at the same time, so that it is possible to apply a large output force to the output shaft 11.

In explaining of the replacement brush 2, as shown in FIGS. 1 and 2, a bristle implantation base 4 in which the brush 3 is implanted is provided and in the base 4 there is formed a fitting hole 5 into which an upper end portion of the output shaft 11 is fit. By fitting the upper end portion of the output shaft 11 to the fitting hole 5 and engaging a looseness stopper pin 11a of the output shaft 11 with a fitting slit 6 of the bristle implantation base 4, the replacement brush 2 can be firmly fit to the output shaft 11.

A shape and weight of a combined body of the output shaft 11, fixture 30, driven magnetic body 31 and replacement brush 2, i.e., vibrating members, are so set that the resonant frequency of this combined body is substantially the same as the frequency of a varying magnetic field generated between both magnetic bodies 23 and 31 as described later. Further, it is preferable to elastically support this combined body substantially corresponding to its center of gravity in order to efficiently vibrate the replacement brush.

Next, an operation and effect of the electric toothbrush 1 will be described.

If the rotating body 22 is rotated by turning on the switch button 20, the four driving magnetic bodies 23 assembled to the rotating body 22 face the driven magnetic bodies 31 successively and at every time when each driving magnetic body 23 approaches each driven magnetic body 31, a varying magnetic field in which a repulsion (attraction in case that different poles are caused to face each other) between both magnetic bodies 23 and 31 increases is formed and by this varying magnetic field the rotary motion of the rotating body 22 is converted to vibration of the output shaft 11, so that the replacement brush 2 is vibrated left and right at a frequency four times the rotation number of the rotating body 22 with the resonance pin 25 being made a center. Further, as shown in FIGS. 5, 8, by turning the adjusting ring 16, a distance between the driving magnet body 23 and driven magnetic body 31 can be adjusted between L1 and L2. As a result, an intensity of magnetic field acting between the magnetic bodies 23 and 31 is adjusted, thereby adjusting an intensity of the vibration. Consequently, it follows that the tooth is brushed under a state that the replacement brush 2 is vibrated with an appropriate intensity.

In this manner, since the output shaft 11 is vibrated by a rotary force of the rotating body 22 through the varying magnetic field with the output shaft 11 side and the rotating body 22 side being kept in non-contacting state, even if an excessive load is applied to the replacement brush 2 during brushing, no excessive load is applied to the electric motor 14. Moreover, since the output shaft 11 is vibrated not mechanically by gear, cam or the like, no large noise is produced. Further, since the casing 12 itself is not vibrated, there is not a loss of vibration to the casing 12 and unpleasant feeling is not given to hand fingers griping the casing 12.

Figure 9:
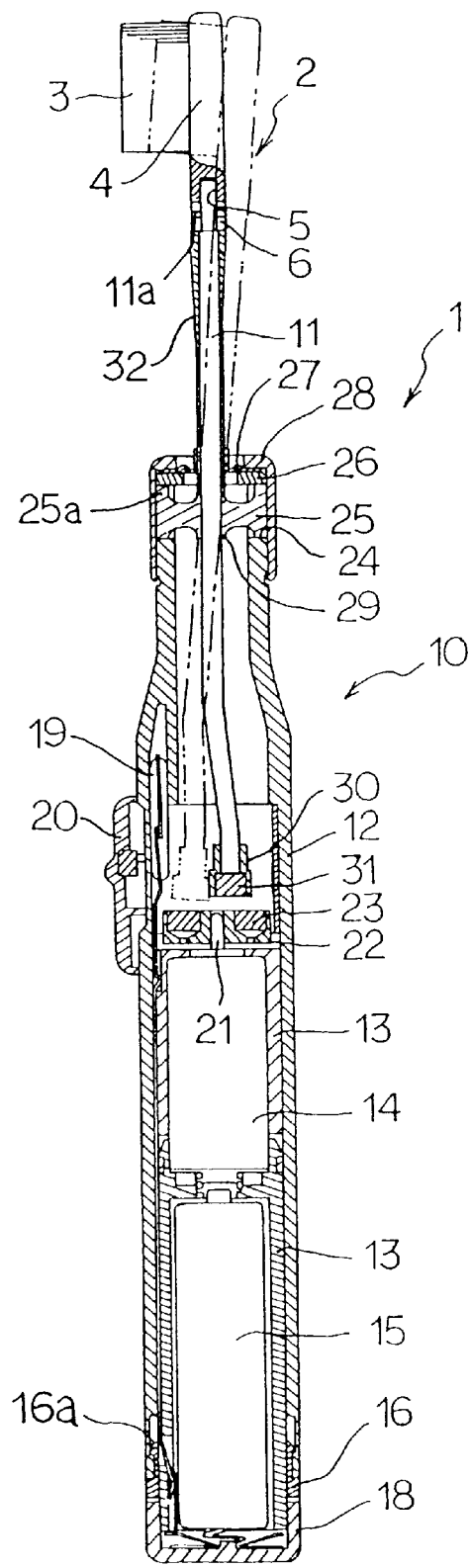
FIG. 9 is a longitudinal sectional view of a portion in the vicinity of an output shaft of an electric toothbrush according to another embodiment in which the structure of the output shaft is partially modified.

Further, since the output shaft 11 is vibrated by the varying magnetic field, no unreasonable force is applied to the gingiva or the like, thereby realizing a soft brushing. Moreover, if the brushing pressure becomes high, the driven magnetic body 31 moves to a side of the rotary shaft 21 of the electric motor 14 as shown by a phantom line in FIG. 1, so that a distance between the driving magnet body 23 and the driven magnetic body 31 is increased, thereby weakening the vibration of the replacement brush 2. As a result, a disadvantage that the gingiva or the like may be injured can be more effectively prevented. However, since there is a user's request that he/she wants to brush strongly when the brushing pressure is high, as shown in FIG. 9, it is also possible to dispose the driven magnetic body 31 so as to face a center side of the electric motor 14 so that when the brushing pressure becomes high, the driven magnetic body 31 faces the drive magnetic field 23 as shown by a phantom line.

Further, since the resonant frequency of the combined body is set to substantially the same as the frequency of the varying magnetic field generated between both magnetic bodies 23 and 31, the amplitude of the output shaft 11 can be sufficiently increased (e.g., 4 mm in both ways), so that the vibration can be transmitted effectively and magnetic loss is decreased.

Next, another embodiment in which the structure of the electric toothbrush 1 is partly modified will be described. Incidentally, the same reference numeral is attached to the same component as the aforementioned embodiment and a detailed description thereof is omitted.

Figure 10:
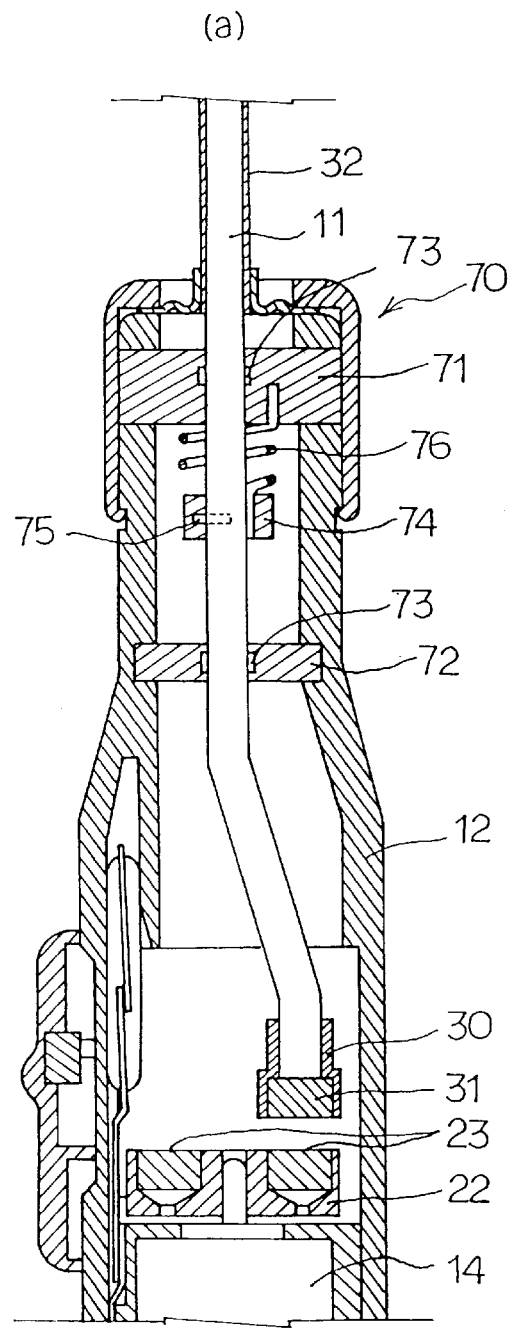
FIG. 10(*a*) is a longitudinal sectional view of a portion in the vicinity of the output shaft of the electric toothbrush according to another embodiment.
Figure 10:
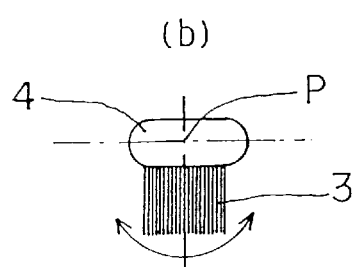

(1) Instead of the resonance pin 25, a resilient member for elastically supporting the output shaft 11 so as to be rotatable in reciprocating way around an axis thereof is provided. And, as shown in FIG. 10(b), it is also possible to set the vibration direction of the replacement brush 2 in a rotating direction with an axis P of the bristle implantation base 4 being made its center. For example, the following structure may be adapted. That is, as in a vibration generating device 70 shown in FIG. 10(a), an intermediate portion of the output shaft 11 is rotatably supported by a pair of upper and lower bearing members 71, 72 through a bearing piece 73 such as ball bearing or bearing metal made of synthetic resin having a low sliding resistance or of metal. A joint member 74 is fixed to the output shaft 11 between the bearing members 71 and 72 via a pin member 75, and an elastic member 76 made of metal having an elasticity or consisting of a twisted spring of synthetic resin is provided and one end thereof is fixed to the joint member 74 and the other end thereof is fixed to the bearing member 71 or bearing member 72 or casing 12. However, it follows that a movement of the output shaft 11 in the axial direction is restricted by the elastic member 76 or bearing device 73 or by forming a flange portion or the like at the intermediate portion of the output shaft 11, which comes into contact with the bearing members 71 and 72.

In such a vibration generating device 70, since the brush 3 is rolled in the reciprocating way as shown in FIG. 10(b), a brushing by rolling process can be carried out easily only by making the brush 3 into contact with the teeth.

Figure 11:
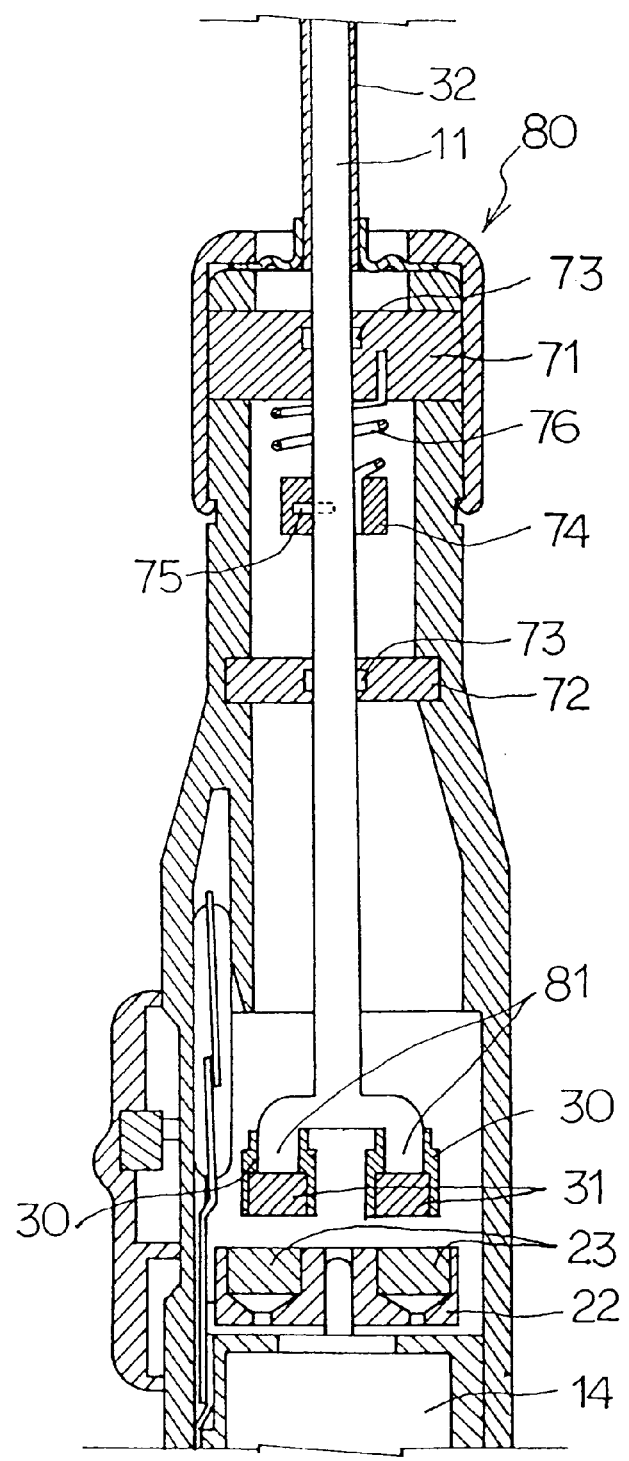
FIG. 11 is a longitudinal sectional view of a portion in the vicinity of an output shaft of an electric toothbrush according to still another embodiment.

Incidentally, like a vibration generating device 80 shown in FIG. 11, it is permissible that the output shaft 11 is formed in a straight form and a lower end portion of the output shaft 11 is branched to two portions and a driven magnetic body 31 is mounted on each lower end portion of the two branched portions 81 so as to face the drive magnetic body 23. In this case, application of an eccentric load to the bearing piece 73 is prevented, thereby preventing eccentric wearing of the bearing device 73 and smoothing the reciprocating rolling of the output shaft 11, so that it become possible to effectively transmit a torque. Moreover, since the lower portion of the output shaft 11 does not have to be inclined, the casing 12 can be formed in a small size in the radial direction and lengthwise direction, so that a compact vibration generating device 80 can be realized.

Figure 12:
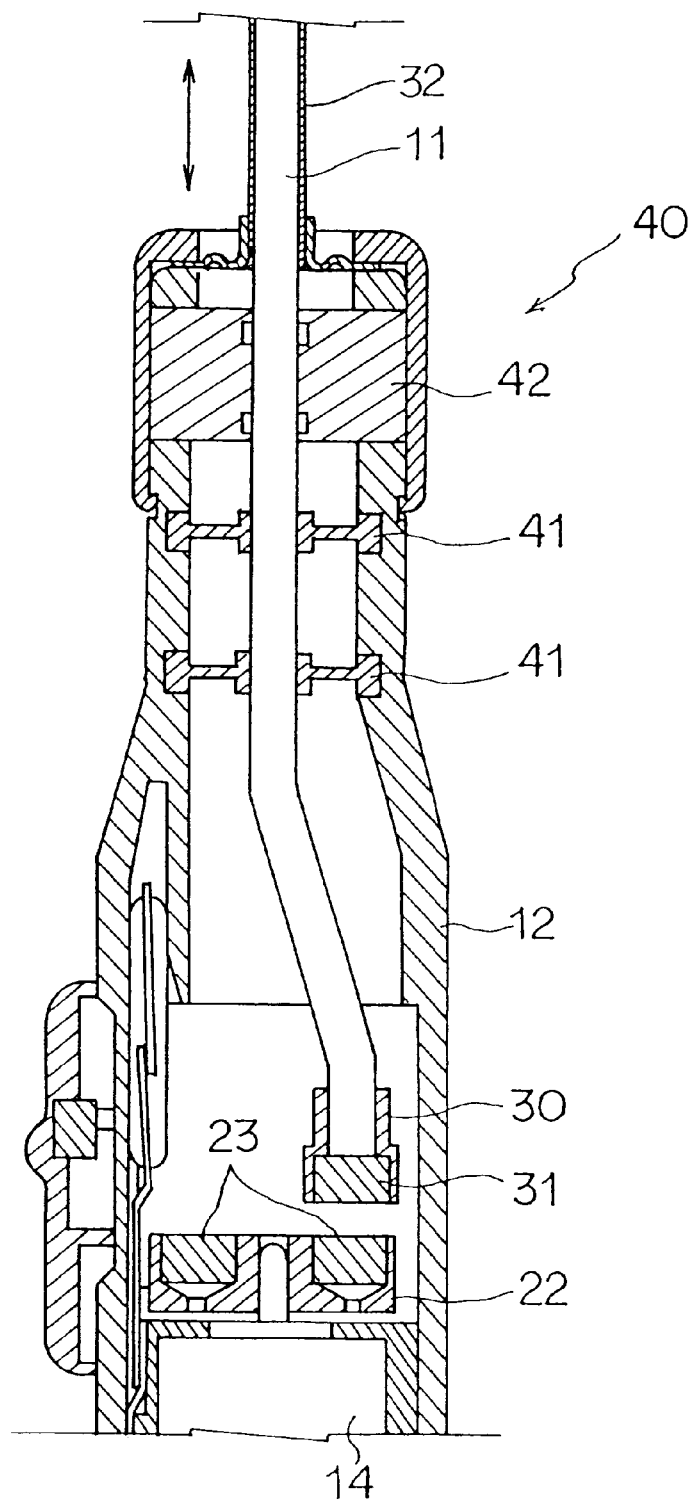
FIG. 12 is a longitudinal sectional view of a portion in the vicinity of the output shaft of the electric toothbrush according to further another embodiment.

(2) The vibration direction of the replacement brush 2 can be set in the vertical direction. For example, like a vibration generating device 40 shown in FIG. 12, instead of the resonance pin 25, a pair of substantially circular upper and lower diaphragms 41 made of highly elastic material such as rubber or of synthetic resin or metal having a spring characteristic are provided and the output shaft 11 is inserted through and fixed to central portions of these diaphragms 41. And in an upper side of the diaphragm 41, the output shaft 11 is guided through a slide bearing 42 so as to be movable vertically relative to the casing 12. In this case, only a vertical movement component of the output shaft 11 in the vertical direction of a repulsion or an attraction acting between the driven magnetic body 31 and the driving magnetic body 23 through the diaphragm 41 and the slide bearing 42 is allowed and it follows that the replacement brush 2 vibrates vertically.

Figure 13:
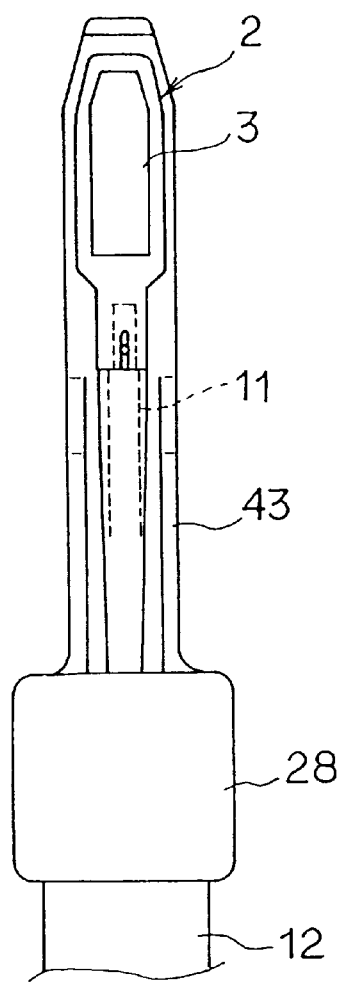
FIG. 13(*a*) is a front view of a portion in the vicinity of an output shaft of an electric toothbrush according to other embodiment.
Figure 13:
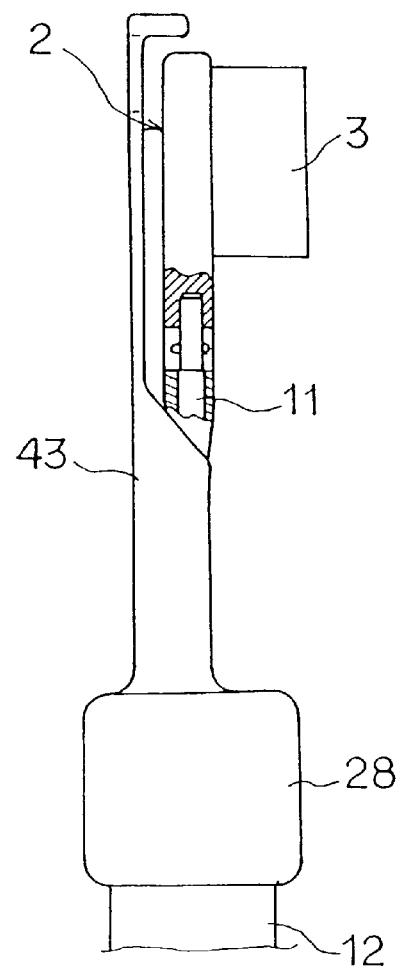

(3) As shown in FIG. 13, by forming on the cap member 28 a cover portion 43 for covering the output shaft 11 and disposing an upper portion of this cover portion 43 up to a rear surface side of the replacement brush 2, an injury of mucous membrane in the oral cavity, which occurs by the fact that the replacement brush 2 directly contact with the mucous membrane, may be prevented.

(4) Although the driving magnet bodies 23 are assembled to an upper face portion of the rotating body 22, it is permissible to mount the driving magnet body 23 on a peripheral surface portion of the rotating body 22 and dispose the driving magnetic body 31 so as to face the driving magnetic body 23 by extending a lower end portion of the output shaft 11 to a periphery side of the rotating body 22.

(5) Although depiction is omitted, in case that an electromagnet is used as the driven magnetic body 31, in order to prevent a lead wire for turning on electricity to the electromagnet from being broken, it is preferable to perform wiring by fixing the lead wire along the output shaft 11 from the electromagnet and extending it from the resonance pin 25 having the least motion to a casing 12 side. Further, in case that an electromagnet is used as the driving magnetic body 23, it follows that a sliding brush which makes a sliding contact with the rotating body 22 is used for turning on electricity. In this manner, if the electromagnet is used as the driven magnetic body 31 or the driving magnet body 23, driving/stopping or the like can be easily controlled from outside and, in addition, it becomes possible to continuously adjust an intensity of vibration by changing magnetic force.

Figure 14:
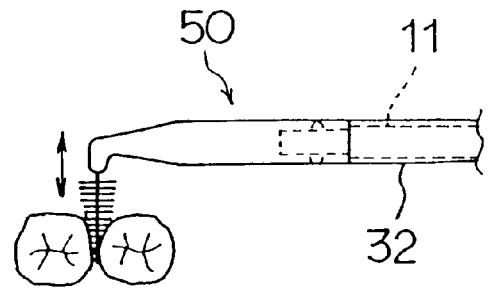
FIG. 14 is a side view of an interdental cleaning tool which can be attached to the vibration generating device of the present invention.
Figure 15:
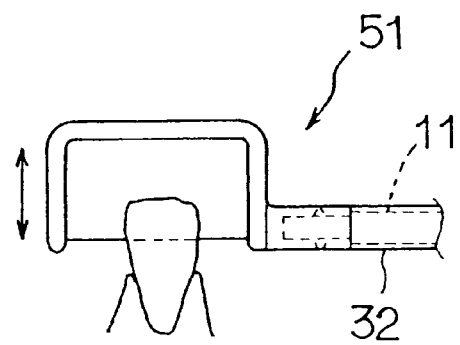
FIG. 15 is a side view of an interdental floss which can be attached to the same vibration generating device.
Figure 16:
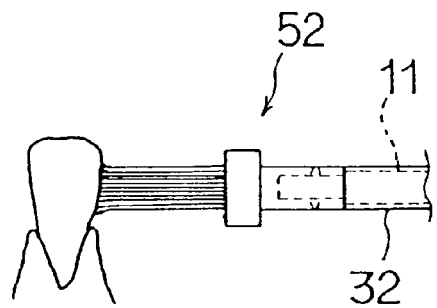
FIG. 16 is a side view of a tool for aesthetically finishing a tooth face, which can be attached to the same vibration generating device.
Figure 17:
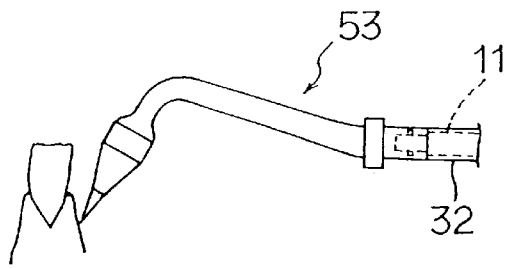
FIG. 17 is a side view of a tool for massaging a gingiva, which can be attached to the same vibration generating device.
Figure 18:
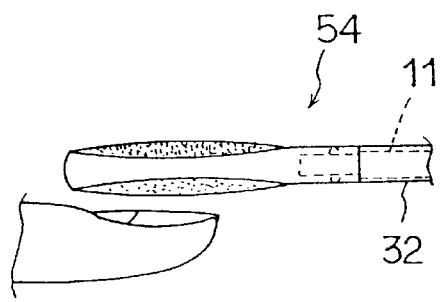
FIG. 18 is a side view of a nail polisher which can be attached to the same vibration generating device.
Figure 19:
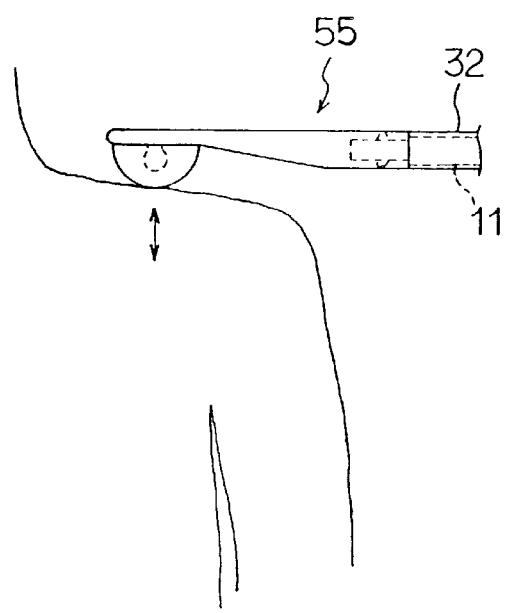
FIG. 19 is a side view of a shoulder tapping tool which can be attached to the same vibration generating device.
Figure 20:
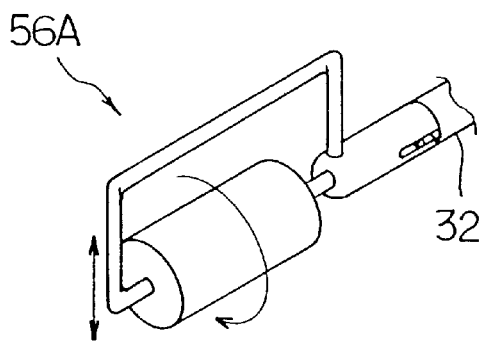
FIGS. 20(*a*), (*b*), (*c*) are perspective views of a face massager which can be attached to the same vibration generating device.
Figure 20:
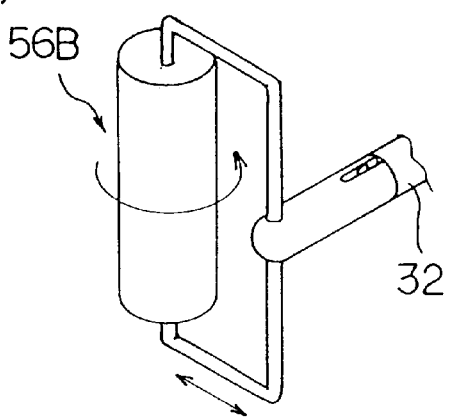
Figure 20:
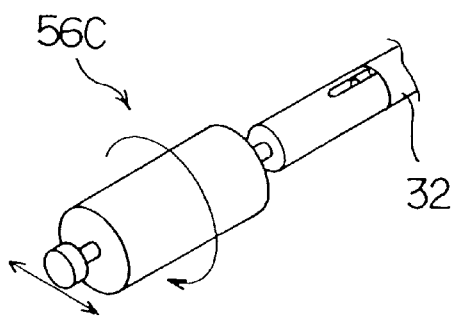

Incidentally, in the above embodiments, although the present invention is applied to the electric toothbrush 1, instead of the replacement brush 2, it is possible to provide various functions by removably mounting to the output shaft 11 of the vibration generating device 10, for example, an interdental brush 50 as shown in FIG. 14, an interdental floss 51 as shown in FIG. 15, a tooth 52 for aesthetically finishing a tooth face as shown in FIG. 16, a tool 53 for massaging a gingiva as shown in FIG. 17, a nail polisher 54 as shown in FIG. 18, a shoulder tapping tool 55 as shown in FIG. 19, face massagers 56A, 56B, 56C as shown in FIG. 20, or and the like.

Figure 21:
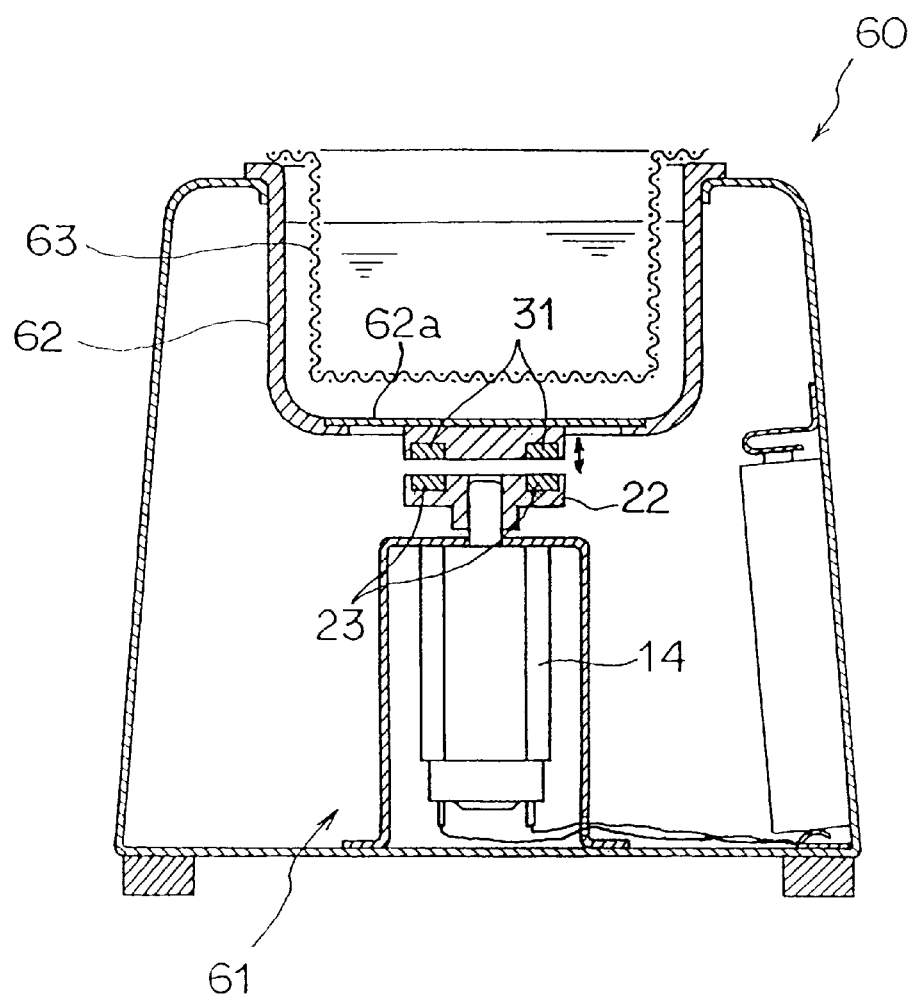
FIG. 21 is a longitudinal sectional view of a cleaning apparatus in which the vibration generating device of the present invention has been incorporated.
Figure 22:
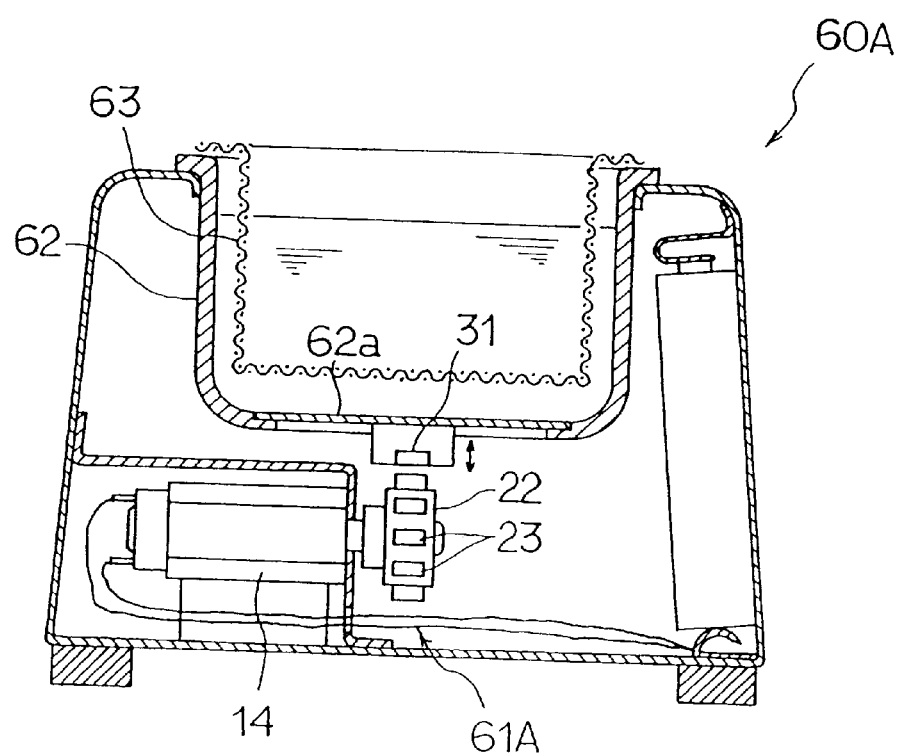
FIG. 22 is a longitudinal sectional view of a cleaning apparatus according to another embodiment.

Further, the present invention can be applied also to various vibration generating devices other than those exemplified above. For example, as shown in FIG. 21, in case that the present invention is applied to a vibration generating device of a cleaning apparatus 60, an opening portion is formed on a bottom or side of a cleaning bath 62 and a membrane body 62a having an elasticity and made of silicone or the like is provided so as to close this opening portion. The driven magnetic bodies 31 are attached to the membrane body 62a and the driving magnet bodies 23 are disposed so as to face these driven magnetic bodies 31. These driving magnetic bodies 23 are rotated together with the rotating body 22 by the electric motor 14 so as to vibrate the membrane body 62a, thereby washing such a small object as glasses immersed in the cleaning bath 62. Incidentally, reference numeral 63 denotes a basket for picking up such a small object as glasses from the cleaning bath 62. Further, as shown in FIG. 22, like a vibration generating device 61A of a cleaning apparatus 60A, it is permissible to assemble the driving magnet bodies 23 to an outer peripheral portion of the rotating body 22 and dispose the driven magnetic body 31 so as to face them.

INDUSTRIAL UTILIZABILITY

According to the vibration generating device of the present invention, by the vibration generating device having a simple structure comprising a rotating body provided with a driving magnetic body, an output member provided with a driven magnetic body, an electric motor for rotating the rotating body and the like, a varying magnetic field is acted between both magnetic bodies to thereby vibrate the output member, so that it becomes possible to effectively transmit vibration to the output member while reducing production cost of the vibration generating device. Further, by changing the numbers of the driving magnetic bodies and the driven magnetic bodies, the frequency of the output member can be changed. Furthermore, since the output member is vibrated through the varying magnetic field, even if a high load is applied to the output member, the electric motor idles, so that there never occurs such a case that the electric motor is overloaded and damaged.

If constituted as recited in claim 2, it becomes possible that both magnetic bodies are disposed as nearly as possible while preventing a contact therebetween, so that it becomes possible to apply a large repulsion to the driven body to thereby strongly vibrate the output member.

If constituted as recited in claim 3, since the combined body is resonated by the varying magnetic field, it becomes possible that the rotary motion of the rotating body can be efficiently converted to vibration of the output body and the amplitude of the combined body is set large.

If constituted as recited in claim 4, it becomes possible that by changing the distance between both magnetic bodies by means of the adjusting means, the vibration of the output member can be intensified or weakened.

If constituted as recited in claim 5, it becomes possible that by appropriately setting the attaching position of the driving magnetic body with respect to the rotating body, the varying magnetic field can be generated easily between the driving magnetic body and the driven magnetic body.

If constituted as recited in claim 6, since it follows that the output member is vibrated with its center being set to a position substantially corresponding to center of gravity of the combined body, the rotating motion of the rotating body can be effectively converted to vibration of the output member.

If constituted as recited in claim 7, it becomes possible that the output member, the rotating body and the electric motor can be compactly constituted in the radial direction of the rotating axis, so that a form preferable for use in gripping by the hand can be realized. Further, since the tip portion of the shaft as an output member is greatly vibrated, by attaching an oral hygiene tool to the tip portion of this shaft, it becomes possible to utilize it while vibrating it.

If constituted as recited in claim 8, it becomes possible that the output member is vibrated at a frequency twice the rotation number of the electric motor.

According to the oral hygiene device of the invention, since an oral hygiene tool is attached to the output member of the vibration generating device recited in any of claims 1–8, an oral hygiene device which is cheap and whose performance is good can be realized.

What is claimed is:

1. An oral hygiene device comprising:

an electric motor installed in a casing and a rotating body mounted on a rotary shaft of the electric motor, a driving magnetic body made of permanent magnet provided in the rotating body, an output member passing through the casing in fluid-tight condition, a resonance pin resiliently supporting a middle portion of the output member to the casing so as to be swingable finely, a driven magnetic body made of permanent magnet provided in the output member to face said driving magnetic body so as not to contact therewith inside the casing, and an oral hygiene tool being removably attached directly or indirectly to the output member outside the casing, wherein the oral hygiene tool through the output member is vibrated by a varying magnetic field generated between both magnetic bodies with a rotation of the rotating body.

2. An oral hygiene device recited in claim 1, wherein the driving magnetic body and the driven magnetic body are arranged such that the same poles thereof face each other.

3. An oral hygiene device recited in claim 1 or 2, wherein the frequency of the varying magnetic field is set to a resonant frequency of a combined body consisting of the output member and the oral hygiene tool.

4. An oral hygiene device recited in claim 1 or 2, wherein there is provided an adjusting means for adjusting a distance between the driving magnetic body and the driven magnetic body.

5. An oral hygiene device recited in claim 1 or 2, wherein the driving magnetic body is fixed eccentrically from a rotary axis of an electric motor and the driven magnetic body is provided so as to face a rotating locus of the driving magnetic body.

6. An oral hygiene device recited in claim 1 or 2, wherein an elastic supporting point of the output member is set at a position substantially corresponding to a center of gravity of the combined body consisting of the output member and the oral hygiene tool.

7. An oral hygiene device recited in claim 1 or 2, wherein as the output member there is used a shaft whose tip side portion is disposed on the same axis as the rotary axis of the electric motor and whose intermediate portion is bent at a base end side than the elastic supporting point such that the driven magnetic body fixed to a based end portion faces a rotating locus of the driving magnetic body.

8. An oral hygiene device recited in claim 1 or 2, wherein two permanent magnets are provided as the driving magnetic body and one permanent magnet is provided as the driven magnetic body.

* * * * *